United States Patent [19]
Rosenthal

[11] 4,189,465
[45] Feb. 19, 1980

[54] METHOD FOR INHIBITING NITROSAMINE FORMATION

[75] Inventor: Maurice L. Rosenthal, New York, N.Y.

[73] Assignee: Robeco Chemicals, Inc., New York, N.Y.

[21] Appl. No.: 903,817

[22] Filed: May 8, 1978

[51] Int. Cl.² .................. A61K 9/06; A61K 47/00
[52] U.S. Cl. .................................. 424/10; 424/355
[58] Field of Search ............................ 424/10, 355

[56] References Cited
PUBLICATIONS

Ogiwara et al.-Chem. Abst. vol. 81 (1974), p. 126,692t.
Kagaku-Chem. Abst. vol. 71 (1969), p. 24698a.
Rao et al.-Chem. Abst. vol. 68 (1968), p. 115,877n.
Uedo et al.-Chem. Abst. vol. 72 (1970), p. 6194z.

Primary Examiner—Sam Rosen
Attorney, Agent, or Firm—Anthony Lagani, Jr.

[57] ABSTRACT

Nitrosamine formation in topical products is inhibited by the addition of an unsaturated hydrocarbon having at least one double bond to the composition at at least one percent by weight based on the overall composition. The preferred unsaturated hydrocarbon is squalene.

4 Claims, No Drawings

METHOD FOR INHIBITING NITROSAMINE FORMATION

BACKGROUND OF THE INVENTION

Nitrosamines have been implicated as carcinogens causing liver tumors in rats. It is well known that secondary amines in the presence of nitrosating agents are converted to nitrosamines. Primary and tertiary amines convert to secondary amines under certain conditions i.e. in the presence of catalyzing agents such as formaldehyde. Nitrates, nitrites and other oxides of nitrogen react readily under such conditions to form nitrosamines. Since nitrogen compounds, including nitrites, are ubiquitous in nature, there is presented the possiblity of nitrosamine formation wherever amine compounds are present.

It is not known whether topically applied products (creams, lotions etc.) containing nitrosamines will in fact cause carcinogenicity. Our present laws are such, however, that any product known to produce any type of cancer in any animal is under scrutiny. As a result, investigators are actively studying the potentially carcinogenic effect of the topical application of products containing nitrosating agents. It would of course be desirable to be able to prevent the formation of such carcinogens in topically applied products.

Certain compounds are known to act as prophylactics in preventing the formation of nitrosamines. In the meat industry the conversion of amines of nitrosamines has been overcome to a great extent by the addition of inhibitors to meat products. The primary inhibitor used is ascorbic acid. Other inhibitors are alpha tocopherol, ascorbyl palmitate, ascorbates and isoascorbates.

It is known that inorganic nitrates and nitrites are unstable oxidizers at elevated temperatures and when in contact with organic materials their acidic decomposition products are likely to become reactive in situ. Some unsaturated hydrocarbons, in particular those having more than one non-conjugated double bond are easily attacked by these acidic products as well as the salts with weak bases. This effect was applied to the stabilization of an ammonium nitrate propellant system where the unsaturated hydrocarbons used included digeranyl, squalene and lycopersen. See for example U.S. Pat. No. 3,215,573 incorporated herein by reference.

SUMMARY OF THE INVENTION

It has surprisingly been found that when an unsaturated hydrocarbon having at least one double bond is incorporated into topical products such as dermatologicals, cosmetics, vaginal creams and toiletries, it inhibits the formation of nitrosamines. The preferred unsaturated hydrocarbon is squalene.

DETAILED DESCRIPTION

This invention relates to a method for inhibiting the conversion of amines and related nitrosating agents to nitrosamines and other known carcinogenic nitrogen compounds. More particularly it relates to the inhibition of the formation of such compounds in topical products such as dermatologicals, cosmetics, vaginal creams and other toiletries intended to be applied to human skin or mucous membrane by the addition to such compounds of an unsaturated hydrocarbon.

In view of the ubiquitous nature of nitrosating agents the formation of nitrosamines may unexpectedly occur even in compositions to which such agents have not been intentionally added. It has been found that the addition of an unsaturated hydrocarbon having at least one double bond to topical products will inhibit the formation of nitrosamines.

Illustrative of the unsaturated hydrocarbons of this invention are digeranyl, squalene and lycopersen. Additionally, natural products such as olive oil, vegetable oils, palm oil, etc. contain such unsaturated hydrocarbons. The preferred unsaturated hydrocarbon is squalene which is itself contained in the aforementioned natural products as well as fish oils.

Squalene is an ubiquitous product occurring in plants, animals and man. It is found in small quantities in vegetable oils and in larger amounts in certain fish oils. Squalene as used in the specification and claims means 2, 6, 10, 15, 19, 23 hexamethyl 2, 6, 10, 14, 18, 22 -tetracosahexaene and has the structural formula

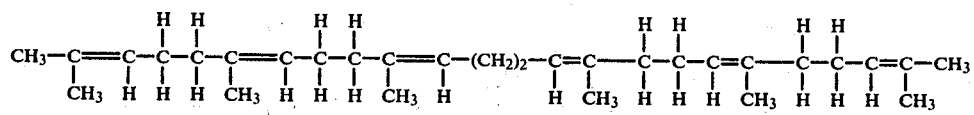

The triterpene, Squalene, is a highly unsaturated aliphatic hydrocarbon ($C_{30}H_{50}$) having six double bonds per molecule. The term terpene hydrocarbon refers to numerous $C_{10}H_{16}$ hydrocarbons and their hydrogenated derivatives with similar basic chemical structures. Many of these carbon skeltons consist of multiples of the isoprene nucleus ($C_5H_8$). Acyclic terpenes are open chain olefinic structures formed by the union of two or more isoprene units. Thus squalene can be termed an acyclic polyisoprene triterpene aliphatic unsaturated hydrocarbon with six unconjugated double bonds. It is found in human sebaceous secretions and is the principal hydrocarbon of human surface lipids amounting to 11 percent of the total surface fat.

Squalene is miscible with vegetable and mineral oils, organic solvents, lipophilic substances and human sebum. It has the following physical and chemical properties.

Mol Wt. 410.73; C 87.73%; H 12.27%; ACID No. 0–5; S/G 20°C., 0.855–0.865;

Iodine No. 360–380; B.P.ca 335° C.; Saponification No. 0–5; Visc. (25° C.) 12 cps.

In toxicological studies no deaths occurred in rats which were fed, by oral administration, up to 37.5 ml/kg. of squalene. In primary skin application on rabbits of 0.5 ml for 72 hours, no erythema, eschar or edema was produced. It is known to impart suppleness to skin and readily forms emulsions with fixed oils and lipophilic substances. It also has the ability to enhance skin respiration to contribute to moisturizing. Hence squalene is a unique raw material which is ideally suited as a constituent of topical products.

In attempting to assign a specific role to squalene in biochemical processes, many interesting phenomenon have been observed. Squalene has been shown to be fungistatic in vitro against certain dermatophytes; see Sobel and Arzangovlian, *Science*, 119, 3101 (1954). Investigations of the fungistatic effect of sebum on skin surfaces led to the observation that certain carcinogenic chemicals are inactivated when exposed to squalene over a period of time. Further studies on patients with epidermoid carcinoma suggests that squalene serves as a protective agent in human sebum. Patients with squamous cell carcinoma were found to have less squalene than individuals from a similar age group who were free of skin lesions. Epidermoid carcinoma is the usual type of carcinoma which arises after exposure to carcinogenic hydrocarbons, excessive exposure to sunlight and ultraviolet rays.

Its utility in inhibiting nitrosamine formation may be more readily appreciated by reference to the following examples.

In the practice of this invention, squalene is added to the topical product at about 1 to about 50 weight percent based on the overall composition; more preferably about 2 to about 40 weight percent; most preferably about 5 to about 30 weight percent; e.g. 28%. As used in the specification and claims, the term "topical product" means dermatologicals, cosmetics, vaginal creams, toiletries and other products intended for application to the human skin and mucous membranes.

The amount of squalene necessary for inhibition of the nitrosamine formation will depend on the concentration of amines, nitrates and nitrites in the formulation. Since often these compounds are not added intentionally, they are there in small quantities. Hence, at least 1% by weight; preferably at least 2% by weight of squalene can be included. The squalene, however, has utility as the oil phase of topical products and can represent the entire oil phase component. Hence, in the formulation shown in the following examples, the squalene, which is a saturated product prepared from the hydrogenation of squalene, may be replaced by squalene.

The squalene is used here as the oil phase of the topical product. In such products any oil which is not toxic or cause allergic reactions may be used. A commonly used oil is mineral oil. Where squalene is incorporated into a product it may be used as the sole oily component.

The term "squalene" as used in the specification and claims includes derivatives of squalene such as partially hydrogenated squalene. The partially hydrogenated compounds have at least one site of unsaturation in the molecule.

The present technology being used to detect, identify and quantify the presence of nitrosamines and particularly N-nitrosodiethanolamine is a sensitive analyzer called Thermal Energy Analyzer.

EXAMPLE I

The following formulations were prepared wherein there has been included Triethanolamine as the amine and 2-Bromo-2-Nitro Propane-1, 3-Diol (Bronopol) as a preservative. The Bronopol acts as the nitrosating agent. The oil phase ingredient is squalene. All constituents are shown as parts per hundred based on total product and sufficient water was added to make up 100 parts by weight of total product.

| A. | CREAM (liquid cleansing) | | C. | LOTION (hand) | |
|---|---|---|---|---|---|
| | Stearic Acid | 4 | | Steric Acid | 3.0 |
| | Squalane | 28 | | Synthetic Spermaceti | |
| | Glycerin | 1 | | & Stearamide DEA | 1.0 |
| | Triethanolamine | 1 | | Lanolin (Anhyd) | 1.0 |
| | Preservative | | | Squalane | 3.0 |
| | (Bronopol) | 0.2 | | Glycerin | 4.0 |
| | Water | QS | | Preservative | |
| | | | | (Bronopol) | 0.2 |
| | | | | Water | QS |
| B. | CREAM (hand) | | D. | LOTION (cleansing) | |
| | Stearic Acid | 7 | | Lanolin anhyd | 2 |
| | Squalane | 2 | | Stearic Acid | 2 |
| | Synthetic Spermaceti | | | Synthetic Spermaceti | |
| | & Stearamide DEA | 2 | | & Stearamide DEA | 1 |
| | Myristyl Lactate | 1 | | Mineral Oil | 35 |
| | Glycerin | 5 | | POE Sorbitan Mono | |
| | Triethanolamine | 1 | | Stearate | 1.5 |
| | Preservative | | | Sorbitan Mono | |
| | (Bronopol) | 0.2 | | Laurate | 1.0 |
| | Water | QS | | Cetyl Alcohol | 0.5 |
| | | | | Squalane | 15.0 |
| | | | | Triethanolamine | 1.0 |
| | | | | Glycerin | 5.0 |
| | | | | Preservative | |
| | | | | (Bronopol) | 0.2 |
| | | | | Water | QS |

The composition is tested after thirty days of standing at room temperature and is found to contain N-nitrosodiethanolamine.

EXAMPLE II

The experiment of Example I is repeated except that at least a part of the squalene is replaced by squalene.

| A. | CREAM (liquid cleansing) | | C. | LOTION (hand) | |
|---|---|---|---|---|---|
| | Stearic Acid | 4 | | Stearic Acid | 3.0 |
| | Squalane | 20 | | Synthetic Spermaceti | |
| | Squalene | 8 | | & Stearamide DEA | 1.0 |
| | Glycerin | 1 | | Lanolin (Anhyd) | 1.0 |
| | Triethanolamine | 1 | | Squalane | 1.0 |
| | Preservative | | | Glycerin | 4.0 |
| | (Bronopol) | 0.2 | | Squalene | 2.0 |
| | Water | QS | | Preservative | |
| | | | | (Bronopol) | 0.2 |
| | | | | Water | QS |
| B. | CREAM (hand) | | D. | LOTION (cleansing) | |
| | Stearic Acid | 7 | | Lanolin anhyd | 2 |
| | Squalane | 2 | | Stearic Acid | 2 |
| | Synthetic Spermaceti | | | Synthetic Spermaceti | |
| | & Stearamide DEA | 2 | | & Stearamide DEA | 1 |
| | Myristyl Lactate | 1 | | Mineral Oil | 35 |
| | Glycerin | 5 | | POE Sorbitan Mono | |
| | Triethanolamine | 1 | | Stearate | 1.5 |
| | Preservative | | | Sorbitan Mono | |
| | (Bronopol) | 0.2 | | Laurate | 1.0 |
| | Water | QS | | Cetyl Alcohol | 0.5 |
| | | | | Squalane | 5.0 |
| | | | | Triethanolamine | 1.0 |
| | | | | Squalene | 10.0 |
| | | | | Glycerin | 5.0 |
| | | | | Preservative | |
| | | | | (Bronopol) | 0.2 |
| | | | | Water | QS |

When tested for nitrosamines, the compositions will show no nitrosamine formation.

Although this invention has been described in terms of preventing the formation of nitrosamines in topical products, it is readily evident from the foregoing results that the unsaturated hydrocarbons may be used to inhibit nitrosamine in any product for human consumption. In particular, squalene may be added to foods such as meats to inhibit nitrosamine formation.

The topical products of this invention generally include, in addition to the oily phase, water, emulsifying agents, wetting agents, waxes and preservatives. However, the compounds may include primarily the oily phase and be free of water and emulsifiers. The particular additives used will depend on the intended applications. Formulations for such topical products are well known in the art and do not form a part of this invention per se.

What is claimed is:

1. A method for inhibiting the formation of nitrosamines in topical products containing an amine and a nitrosating agent which comprises incorporating into such products at least one percent by weight of squalene based on the overall composition.

2. The method of claim 1 wherein the squalene is incorporated at at least 2 weight percent.

3. The method of claim 2 wherein the squalene is incorporated at about 2 to about 50 weight percent.

4. The method of claim 1 wherein the squalene is a partially hydrogenated squalene having at least one site of unsaturation.

* * * * *

UNITED STATES PATENT AND TRADEMARK OFFICE
CERTIFICATE OF CORRECTION

PATENT NO. : 4,189,465
DATED : February 19, 1980
INVENTOR(S) : Maurice L. Rosenthal It is certified that error appears in the above—identified patent and that said Letters Patent is hereby corrected as shown below:

Column 3, lines 33 and 34, "squalene" should read -- squalane --.

Column 3, line 37, after "The" the word "squalene" should read -- squalane --.

Column 3, line 58, EXAMPLE I, after 'ingredient is' the word "squalene" should read -- squalane --.

Column 4, line 29, EXAMPLE II, after 'of the' the word "squalene" should read -- squalane --.

Signed and Sealed this

Twenty-seventh Day of May 1980

[SEAL]

Attest:

SIDNEY A. DIAMOND

Attesting Officer

Commissioner of Patents and Trademarks